United States Patent [19]

Marshall et al.

[11] Patent Number: 4,923,801

[45] Date of Patent: May 8, 1990

[54] COMPOSITIONS AND METHODS FOR THE ENRICHMENT AND ISOLATION OF *CAMPYLOBACTER PYLORI* AND RELATED ORGANISMS FROM BIOLOGICAL SPECIMENS AND THE ENVIRONMENT

[75] Inventors: Barry J. Marshall; Richard L. Guerrant, both of Charlottesville, Va.

[73] Assignee: The University of Virginia Alumni Patents Foundation, Charlottesville, Va.

[21] Appl. No.: 37,938

[22] Filed: Apr. 13, 1987

[51] Int. Cl.[5] .................. C12Q 1/58; C12Q 1/04; C12Q 1/34; C12Q 1/24
[52] U.S. Cl. ........................... 435/12; 435/34; 435/18; 435/30; 435/252.1
[58] Field of Search .................. 435/34, 253, 800, 12, 435/18, 29, 30

[56] References Cited
PUBLICATIONS

Washington II, J. A., in *Laboratory Procedures in Clinical Microbiology*, pp. 194–195 (1985).
Goodwin, C. S. et al, CA 103: 192789d, vol. 103, p. 373 (1985).

*Primary Examiner*—Robert J. Warden
*Assistant Examiner*—Toni R. Scheiner
*Attorney, Agent, or Firm*—James Creighton Wray

[57] ABSTRACT

A method of enrichment and isolation of urease producing organisms from a contaminated specimen by first homogenizing the contaminated specimen in water, then introducing the homogenized contaminated specimen into a solution of urea in an acid, wherein some of the organisms are killed by the acidic medium and remaining organisms are protected from acid attack by creating a protective ammonia by breaking down the urea, and plating the remaining organisms onto a medium which contains antibiotics inhibitory to some of the remaining organisms, but not inhibitory to organisms to be isolated.

12 Claims, No Drawings

4,923,801

COMPOSITIONS AND METHODS FOR THE ENRICHMENT AND ISOLATION OF *CAMPYLOBACTER PYLORI* AND RELATED ORGANISMS FROM BIOLOGICAL SPECIMENS AND THE ENVIRONMENT

BACKGROUND OF THE INVENTION

*C. pylori* is a slow growing, fastidious organism and therefore cannot be easily isolated from biologic specimens which contain other contaminating bacteria. The contaminating bacteria in such specimens grow quickly and overgrow any *C. pylori* which may be present. For this reason, *C. pylori* cannot be cultured from the usual specimens such as stool, although it may be isolated from stomach biopsies and gastric juice. These latter two specimens require an expensive endoscopy and biopsy of the stomach. There is a need therefore for a method which might enable *C. pylori* to be isolated from a stool specimen, vomitus, oral secretions, contaminated gastric biopsies or other patient specimens, or specimens from the environment.

DESCRIPTION OF THE INVENTION

Part One of the Invention—Methods for the enrichment and isolation of *Campylobacter pylori* and related organisms from biological specimens and the environment We have discovered that *C. pylori* can survive in an acid medium, provided that urea is present. Other bacteria are killed by acid even when urea is present, but *C. pylori* breaks down the urea to generate ammonia. Ammonia is alkaline and protects the organism from acid attack. This protection comes in two phases. When large amounts of *C. pylori* are inoculated into solutions containing urea with a pH greater than approximately 2.5, the organism is able to modify the pH of the solution and raise it to a more comfortable environment, e.g. pH 6.5. Secondly, if the pH of the solution is less than 2.5, *C. pylori* does not raise the pH of the total solution but still survives, presumably by the action of urease within the organism. *C. pylori* maintains an intracellular or pericellular microenvironment that protects its viability against the surrounding acidic environment.

Utilizing this principle it is possible to isolate *C. pylori* from heavily contaminated specimens such as stool. The sample to be cultured is first homgenized in a small volume of water and then diluted with a solution of urea in acid. This step will obtain an aqueous suspension of the sample in a highly acidic environment in the presence of urea. As an example, in a recent experiment we homogenized five grams of stool in 20 mls of normal saline. The suspension was then inoculated with 0.5mls of saline to which a colony of *C. pylori* had been added. After 10 minutes, the stool/*C. pylori* mixture was added to 4.5 mls of 5 mmolar urea solution which had been acidified to a pH of 1.6 with sulfuric acid. The specimen was then incubated at room temperature for 5 minutes. Samples of the solution were then plated onto non-selective blood agar and cultured in a micro-aerophilic environment for three days. After three days there were very few contaminating organisms on the plate but the *C. pylori* had survived and colonies of the organism were present.

This general principle may be used to isolate any urease producing organism from the environment. The incubation of the specimen in the presence of strong acid and urea is an "enrichment" process which markedly decreases the ratio of contaminating organisms to the urease producing organism. A further enhancement is to plate the specimen after incubation, onto a medium which contains antibiotics inhibitory to organisms which survive the incubation step, but which are not inhibitory to the organism being sought.

Part Two of the Invention—Culture medium for the rapid identification of *C. pylori* and related organisms We have observed that the urease enzyme of *C. pylori* is immediately denatured in strong acid. This process is irreversible. Many other bacterial irease enzymes are also denatured in this way. We have observed that when a specimen that contains *C. pylori* is plated onto a urea detection agar (for example CLOtest agar), there is enough preformed urease in the specimen to react with the agar and produce a color change, even if no bacterial growth occurs. Similarly, a normal stool sample contains some active preformed bacterial urease which causes a color change after some hours in contact with such a urease detection gel. However, if the specimen is ground or homogenized and then acid-treated as in part one of this invention, pre-formed extra cellular urease is destroyed. The specimen may then be plated onto a urea-detecting culture medium. At this point the only active urease will be in live, intact organisms. As the bacteria grow in the selected urease detecting medium, new urease will be produced and will escape from the bacteria within a short time, (less than 48 hours). A bacterial colony producing urease is then visible on the medium by the presence of a color change in the underlying gel. Thus a urease producing organism is detected well before the slow-growing colonies are large enough to see with the naked eye (in the case of *C. pylori* the culture usually takes 3 days). A single colony is easily picked off and sub-cultured. An way to make such a urease detection culture medium is to start with a clear agar on which *C. pylori* grows, such as Brucella or GC agar with the addition of 1% fetal calf or horse serum and 1% corn starch (Buck G. E., Smith J. S. Medium Supplementation for growth of *C. pyloridis*. J Clin Microbiol 1987; 25: 597-99). A suitable addition to this medium is urea in a concentration of between 1-100 mmols per liter, and a pH indicator such as phenol red or thymol blue. A buffer may be added to adjust the final pH of the agar to between 3.0 and 7.0. An example of a suitable buffer is 45 mls of 0.1 molar disodium citrate plus 55 mls of 0.1N HCl as described in Ciba Geigy scientific tables. Acidification of the agar would further enhance the selection of urease positive organisms but may affect the stability of the medium.

An example of this method would be the isolation of *C. pylori* from a gastric biopsy specimen. If the fresh specimen is plated immediately into the urease detecting culture agar, there is enough urease in the specimen to change the color of the medium generally, and prevent the early isolation of a single colony. However, if the biopsy is ground and treated with acid and urease solution for between 1 and 30 minutes and then plated onto the urease detection medium, the only urease present is within live organisms. Very early colonies are then detected by a color change. Similar pre-treatment would enable early isolation of *C. pylori* or other urease producing organisms from a contaminated biological specimen such as stool, sputum, or vaginal secretion, or from the environment. The early detection and subsequent isolation of *C. pylori* would be very useful to enable specific etiologic diagnosis of this infection and rapid determination of antibiotic sensitivities (a process which now takes approximately 7 days in most laboratories).

We claim:

1. A method of enrichment and isolation of *C. pylori* from a specimen contaminated with a plurality of non-urease and urease producing organisms comprising the steps of:
   (a) homogenizing a specimen contaminated with a plurality of organisms in water;
   (b) introducing the contaminated specimen into a solution of urea which has been acidified to a pH of less than 2.5, wherein some of the urease producing and most of the non-urease producing organisms are killed by the acidic medium and remaining urease producing organisms are protected from acid attack by creating a protective ammonia layer by breaking down the urea; and
   (c) plating the remaining urease producing organisms onto a medium which contains antibiotics inhibitory to most of the remaining urease producing organisms, but not inhibitory to the *C. pylori;* and
   (d) detecting the presence of colonies of *C. pylori.*

2. The method of claim 1, wherein the contaminated specimen is a gastric biopsy specimen.

3. The method of claim 1, wherein the contaminated specimen is a stool specimen.

4. A method of enrichment and isolation of *C. pylori* from a specimen contaminated with a plurality of organisms comprising the steps of:
   (a) homogenizing a specimen contaminated with a plurality of organisms in water;
   (b) introducing the contaminated specimen into 5 mls of a 5 mmolar urea solution which has been acidified to a pH of 1.6;
   (c) incubating the solution of step (b) at room temperature for 5-30 minutes;
   (d) plating the incubated solution of step (c) onto a non-selective blood agar;
   (e) culturing the plated solution in a micro-aerophilic environment for three days;
   (f) observing colonies of *C. pylori;* and
   (g) isolating the colonies of *C. pylori* from the blood agar.

5. The method of claim 4, wherein the contaminated specimen is a gastric biopsy specimen.

6. The method of claim 4 wherein the contaminated specimen is a stool specimen.

7. A method of enrichment, isolation and identification of *C. pylori* comprising the steps of:
   (a) homogenizing a specimen contaminated with a plurality of urease and non-urease producing organisms in water;
   (b) introducing the homogenized specimen into a solution of urea which has been acidified to a pH of less than 2.5 for a predetermined time, wherein some of the urease producing and most of the non-urease producing organisms are killed by the acidic medium and remaining urease producing organisms are protected from acid attack by creating a protective layer of ammonia by breaking down the urea;
   (c) plating the solution of step (b) onto a urease detection medium which contains antibiotics inhibitory to most of the remaining urease producing organisms, but not inhibitory to the *C. pylori;*
   (d) detecting color change on the medium which indicates a presence of live *C. pylori* bacteria.

8. The method of claim 7, wherein the specimen in step (b) is a gastric biopsy specimen.

9. The method of claim 7, wherein the medium of step (d) comprises:
   a clear agar in which *C. pylori* grows,
   one percent animal serum selected from the group consisting of calf and horse,
   one percent corn starch,
   urea in a concentration of between 1-100 mmols per liter,
   a pH indicator, and
   a buffer added to adjust a final pH of the agar to between 3.0 and 7.0.

10. The method of claim 8, wherein the gastric biopsy specimen is introduced into the solution of step (c) for between 1-30 minutes.

11. The method of claim 9, wherein the buffer is 45 mls of 0.1 molar disodium citrate plus 55 mls of 0.1N HCl.

12. The method of claim 9, wherein the agar is acidified to further enhance the selection of *C. pylori.*

* * * * *